(12) United States Patent
Blanc et al.

(10) Patent No.: US 12,144,965 B2
(45) Date of Patent: Nov. 19, 2024

(54) AUTOMATED SYSTEM FOR REGULATING THE BLOOD GLUCOSE LEVEL OF A PATIENT

(71) Applicant: Commissariat à l'Énergie Atomique et aux Énergies Alternatives, Paris (FR)

(72) Inventors: Romain Blanc, Grenoble (FR); Eléonore Maeva Doron, Grenoble (FR); Emma Villeneuve, Grenoble (FR)

(73) Assignee: Commissariat à l'Énergie Atomique et aux Énergies Alternatives, Paris (FR)

( * ) Notice: Subject to any disclaimer, the term of this patent is extended or adjusted under 35 U.S.C. 154(b) by 799 days.

(21) Appl. No.: 17/414,901

(22) PCT Filed: Dec. 20, 2019

(86) PCT No.: PCT/FR2019/053237
§ 371 (c)(1),
(2) Date: Jun. 16, 2021

(87) PCT Pub. No.: WO2020/128387
PCT Pub. Date: Jun. 25, 2020

(65) Prior Publication Data
US 2022/0062551 A1    Mar. 3, 2022

(30) Foreign Application Priority Data

Dec. 21, 2018 (FR) .................................. 1873812

(51) Int. Cl.
*A61M 5/172* (2006.01)
*G16H 20/17* (2018.01)
(Continued)

(52) U.S. Cl.
CPC .......... *A61M 5/1723* (2013.01); *G16H 20/17* (2018.01); *G16H 40/63* (2018.01);
(Continued)

(58) Field of Classification Search
None
See application file for complete search history.

(56) References Cited

U.S. PATENT DOCUMENTS 10,332,633 B2 * 6/2019 Duke ..................... G16H 10/40
10,806,859 B2 * 10/2020 Desborough ..... A61M 5/14248
(Continued)

FOREIGN PATENT DOCUMENTS

GB    2 436 873 A1    10/2007

OTHER PUBLICATIONS

International Preliminary Report on Patentability for International Application No. PCT/FR2019/053237, mailed Jul. 1, 2021.
(Continued)

*Primary Examiner* — Manuel A Mendez
(74) *Attorney, Agent, or Firm* — Wolf, Greenfield & Sacks, P.C.

(57) ABSTRACT

An automated system for regulating a patient's blood glucose, including a blood glucose sensor, an insulin injection device, and a processing and control unit.

13 Claims, 5 Drawing Sheets

(51) Int. Cl.
*G16H 40/63* (2018.01)
*G16H 10/60* (2018.01)

(52) U.S. Cl.
CPC ..... *A61M 2205/18* (2013.01); *A61M 2205/50* (2013.01); *A61M 2230/201* (2013.01); *A61M 2230/63* (2013.01); *G16H 10/60* (2018.01)

(56) References Cited

U.S. PATENT DOCUMENTS

| | | | | |
|---|---|---|---|---|
| 2012/0277723 | A1* | 11/2012 | Skladnev | A61M 5/1723 604/504 |
| 2014/0118138 | A1 | 5/2014 | Cobelli et al. | |
| 2019/0216405 | A1* | 7/2019 | Reichel | G16H 50/20 |

OTHER PUBLICATIONS

International Search Report and Written Opinion for International Application No. PCT/FR2019/053237, mailed Apr. 6, 2020.

Hovorka et al., Nonlinear model predictive control of glucose concentration in subjects with type 1 diabetes. Physiological Measurement. Jul. 2, 20042;25(4):905-20.

Hovorka et al. Partitioning glucose distribution/transport, disposal, and endogenous production during IVGTT. American Journal of Physiology-Endocrinology and Metabolism. May 1, 2002;282(5):E992-1007.

Lajeunesse, Software program can predict blood sugar crashes, spikes for patients with type 1 diabetes. Medical Express. https://medicalxpress.com/news/2014-02-software-blood-sugar-spikes-patients.html. Feb. 26, 2014, 3 pages.

* cited by examiner

AUTOMATED SYSTEM FOR REGULATING THE BLOOD GLUCOSE LEVEL OF A PATIENT

This application is a national stage filing under 35 U.S.C. § 371 of International Patent Application Serial No. PCT/FR2019/053237, filed Dec. 20, 2019, which claims priority to French patent application FR18/73812, filed Dec. 21, 2018. The contents of these applications are incorporated herein by reference in their entireties.

TECHNICAL BACKGROUND

The present application relates to the field of automated blood glucose regulation systems, also called artificial pancreases.

PRIOR ART

An artificial pancreas is a system enabling to automatically regulate the insulin inputs of a diabetic patient based on their glycemia (or blood glucose) history, on their meal history, on their insulin injection history.

Examples of regulation systems of this type are particularly described in patent applications WO2018/055283 (DD16959/B15018) and WO2018/055284 (DD17175/B15267) previously filed by the applicant.

It would be desirable to be able to improve the performances of known artificial pancreases, and particularly to be able to further limit risks of placing the patient in a hyperglycemia or hypoglycemia situation.

SUMMARY

Thus, an embodiment provides an automated system for regulating a patient's blood glucose, comprising:
- a blood glucose sensor;
- an insulin injection device; and
- a processing and control unit, wherein the processing and control unit is configured to implement a hypoglycemia minimization method comprising the steps of:
a) detecting a possible hypoglycemia to come based on blood glucose measurements supplied by the blood glucose sensor;
b) determining a value BGdebt representative of a blood glucose debt to be compensated to avoid the hypoglycemia detected at step a) and a value Thypo representative of the time remaining before the beginning of the hypoglycemia detected at step a);
c) determining a value Tautosugaring representative of the time necessary to enable the patient to compensate for the blood glucose debt BGdebt determined at step b) by endogenous glucose production;
d) comparing the value Tautosugaring determined at step c) with a value Thypo-TH, where TH is a predetermined time margin; and
e) controlling the interruption of the insulin flow injected to the patient by the insulin injection device and/or starting an alert via a user interface device of the system to indicate to the patient that they must perform a resugaring when it is determined at step d) that value Tautosugaring is greater than or equal to value Thypo-TH.

According to an embodiment, at step c), the processing and control unit determines a value EGE representative of the patient's endogenous blood glucose rise rate, value Tautosugaring then being calculated by the processing and control unit according to the following formula:

$$Tautosugaring = \frac{BGdebt}{EGE} \quad [\text{Math 1}]$$

According to an embodiment, at step c), value EGE is calculated by the processing and control unit by analysis of the patient's blood glucose history and insulin injection history.

According to an embodiment, at step e), the processing and control unit determines a value predBGΔThypo estimative of the patient's future blood glucose at the end of period Thypo.

According to an embodiment, the processing and control unit is configured to, after step e), implement the steps of:
f) comparing value predBGΔThypo with a predetermined hypoglycemia threshold BGlimhypo;
g) when it is determined at step f) that value predBGΔThypo is smaller than hypoglycemia threshold BGlimhypo, compare a value BG(t0) representative of the patient's current blood glucose, measured by the sensor, with a value BGlimhypo+T1, where T1 is a predetermined blood glucose margin; and
h) when it is determined at step g) that value BG(t0) is smaller than value BGlimhypo+T1, start an alert via a user interface device of the system to indicate to the patient that they must perform a resugaring.

According to an embodiment, at step b), the processing and control unit determines three values Thypolim, Thypomean, and Thypocurrent estimative of the time remaining before the beginning of the hypoglycemia, respectively based on a maximum blood glucose drop rate nGRClim determined for the patient, on an average blood glucose drop rate nGRCmean estimated for the patient, and on a current blood glucose drop rate nGRCcurrent estimated for the patient.

According to an embodiment, the processing and control unit is configured to, at step d), compare duration Tautosugaring with a value ThypoMIN-TH, where ThypoMIN is the shortest of the three durations Thypolim, Thypomean, and Thypocurrent.

According to an embodiment, the processing and control unit is configured to, at step c), calculate three values predBGΔThypolim, predBGΔThypomean, and predBGΔThypocurrent estimative of the patient's future blood glucose respectively at the end of period Thypolim, at the end of period Thypomean, and at the end of period Thypocurrent.

g') if a single one of the three values predBGΔThypolim, predBGΔThypomcan, and predBGΔThypocurrent is smaller than BGlimhypo, suggesting a resugaring to the patient only if a value BG(t0) representative of the patient's current blood glucose is smaller than a value BGlimhypo+T1, where T1 is a predetermined blood sugar margin, if two of the three values predBGΔThypolim, predBGΔThypomean, and predBGΔThypocurrent are smaller than threshold BGlimhypo, suggesting a resugaring to the patient only if value BG(t0) is smaller than a value BGlimhypo+T2, where T2 is a predetermined blood glucose margin greater than margin T1, and if the three values predBGΔThypolim, predBGΔThypomean, and predBGΔThypocurrent are smaller than threshold BGlimhypo, suggesting a resugaring to the patient only if value BG(t0) is smaller than a value BGlimhypo+T3, where T3 is a predetermined blood glucose margin greater than margin T2.

According to an embodiment, the system further comprises a device for measuring a physical activity of the patient coupled to the processing and control unit and communicating to the processing and control unit a signal iap(t) representative of the time variation of a physical activity of the patient.

According to an embodiment, the processing and control unit takes into account signal iap(t) to detect a possible hypoglycemia to come at step a) and/or to determine value Tautosugaring at step c).

According to an embodiment, at step c), the processing and control unit determines a signal IOB(t) representative of the patient's quantity of insulin on board, defined by the multiplication of a signal representative of the quantity of insulin injected to the patient by a decreasing exponential of time constant τIOBap, time constant τIOBap being a decreasing function of signal iap(t), modeling the increase of the speed of action of insulin when the intensity of the physical activity increases.

According to an embodiment, time constant τIOBap is defined as follows:

$$\tau IOBap = \frac{C}{iap(\tau)} \quad \text{[Math 2]}$$

where C is a parameter in the range from 1 to 100.

BRIEF DESCRIPTION OF THE DRAWINGS

The foregoing features and advantages, as well as others, will be described in detail in the following description of specific embodiments given by way of illustration and not limitation with reference to the accompanying drawings, in which.

DESCRIPTION OF THE EMBODIMENTS

Like features have been designated by like references in the various figures. In particular, the structural and/or functional features that are common among the various embodiments may have the same references and may dispose identical structural, dimensional and material properties.

For the sake of clarity, only the steps and elements that are useful for an understanding of the embodiments described herein have been illustrated and described in detail. In particular, the blood glucose measurement devices and the insulin injection devices of the described regulation systems have not been detailed, the described embodiments being compatible with all or most known blood glucose measurement and insulin injection devices. Further, the hardware implementation of the processing and control unit of the described regulation systems has not been detailed, the forming of such a processing and control unit being within the abilities of those skilled in the art based on the functional indications of the present disclosure.

Unless specified otherwise, the expressions "around", "approximately", "substantially" and "in the order of" signify within 10%, and preferably within 5%.

Figure 1:
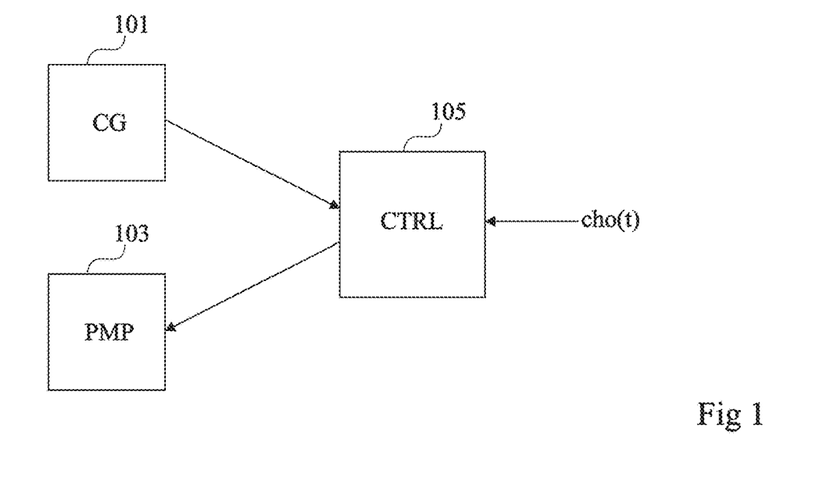
FIG. 1 schematically shows in the form of blocks an example of an automated system for regulating a patient's blood glucose according to an embodiment.

FIG. 1 schematically shows in the form of blocks an embodiment of an automated system of regulation of a patient's blood glucose.

The system of FIG. 1 comprises a sensor 101 (CG) capable of measuring the patient's blood glucose. In normal operation, sensor 101 may be permanently positioned on or inside of the patient's body, for example, at the level of their abdomen. Sensor 101 is for example a CGM-type ("Continuous Glucose Monitoring") sensor, that is, a sensor capable of measuring, continuously or at a relatively high frequency (for example, at least once every twenty minutes and preferably at least once every five minutes) the patient's blood glucose. Sensor 101 is for example a subcutaneous blood glucose sensor.

The system of FIG. 1 further comprises an insulin injection device 103 (PMP), for example, a subcutaneous injection device. Device 103 is for example, an automatic injection device of insulin pump type, comprising an insulin reservoir connected to an injection needle implanted under the patient's skin, and the pump may be electrically controlled to automatically inject determined insulin doses at determined times. In normal operation, injection device 103 may be permanently positioned inside of or on the patient's body, for example, at the level of their abdomen.

The system of FIG. 1 further comprises a processing and control unit 105 (CTRL) connected on the one hand to blood glucose sensor 101. for example, by a wire link or by a radio (wireless) link, and on the other hand to injection device 103, for example, by wire or radio link. In operation, processing and control unit 105 is capable of receiving the data relative to the patient's blood glucose measured by sensor 101, and of electrically controlling device 103 to inject to the patient determined insulin doses at determined times. In this example, processing and control unit 105 is further capable of receiving, via a user interface, not detailed, data cho(t) representative of the time variation of the quantity of glucose ingested by the patient.

Processing and control unit 105 is capable of determining the insulin doses to be injected to the patient by taking into account, in particular, the history of the blood glucose measured by sensor 101, the history of the insulin injected by device 103, and the history of carbohydrate ingestion by the patient. To achieve this, processing and control unit 105 comprises a digital calculation circuit (not detailed), for example comprising a microprocessor. Processing and control unit 105 is for example a mobile device carried by the patient all along the day and/or the night, for example, a smart phone-type device configured to implement a regulation method of the type described hereafter.

Processing and control unit 105 is for example configured to implement an automated MPC-type ("Model-based Predictive Control") regulation method, also called predictive control method, where the regulation of the administered insulin dose takes into account a prediction of the future trend of the patient's blood glucose over time, obtained from a mathematical model, for example, a physiological model describing the assimilation of insulin by the patient's body and its impact on the patient's blood glucose.

More particularly, processing and control unit 105 may be configured to, based on the injected insulin history and on the ingested carbohydrate history, and based on a predetermined mathematical model, determine a curve representative of the expected trend of the patient's blood glucose over time, over a period to come called prediction period or prediction horizon, for example, a period from 1 to 10 hours. Taking this curve into account, processing and control unit 105 determines the insulin doses that should be injected to the patient during the prediction period to come, so that the patient's real blood glucose (as opposed to the blood glucose estimated based on the model) remains within acceptable limits, and in particular to limit risks of hyperglycemia or of hypoglycemia.

In this operating mode, as will be discussed in further detail hereafter, the real blood glucose data measured by sensor 101 are mainly used for purposes of calibration of the mathematical model.

Figure 2:
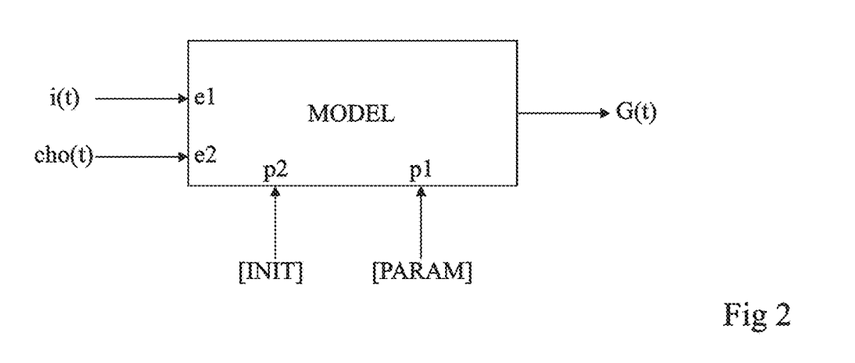
FIG. 2 is a simplified representation of a physiological model capable of being used in the system of FIG. 1 to predict the future trend of the patient's blood glucose.

FIG. 2 is a simplified representation of a mathematical model MODEL used in the system of FIG. 1 to predict the future trend of the patient's blood glucose. In FIG. 2, the model is shown in the form of a processing block comprising:

- an input e1 having a signal i(t) representative of the variation, over time t, of the quantity of insulin injected to the patient, applied thereto;
- an input e2 having a signal cho(t) representative of the trend, over time t, of the quantity of glucose ingested by the patient, applied thereto; and
- an output s delivering a signal G(t) representative of the trend, over time t, of the patient's blood glucose.

Model MODEL is for example a physiological model, for example, a compartmental model comprising, in addition to input variables i(t) and cho(t) and output variable G(t), a plurality of state variables corresponding to physiological variables of the patient, varying over time. The time variation of the state variables and of output variable G(t) is ruled by a differential equation system comprising a plurality of parameters represented in FIG. 2 by a vector [PARAM] applied to an input p1 of block MODEL. The response of the physiological model is further conditioned by the initial states or initial values assigned to the state variables, represented in FIG. 2 by a vector [INIT] applied to an input p2 of block MODEL.

As an example, model MODEL is the physiological model called Hovorka model, described in the article entitled "Nonlinear model predictive control of glucose concentration in subjects with type 1 diabetes" of Roman Hovorka et al. (Physiol Meas. 2004; 25:905-920), and in the article entitled "Partitioning glucose distribution/transport, disposal, and endogenous production during IVGTT", of Roman Hovorka et al. (Am J Physiol Endocrinol Metab 282: E992-E1007, 2002). More generally, any other physiological model describing the assimilation of insulin by a patient's body and its effect on the patient's blood glucose may be used, for example, the model called Cobelli's model, described in the article entitled "A System Model of Oral Glucose Absorption: Validation on Gold Standard Data", of Chiara Dalla Man et al. (IEEE TRANSACTIONS ON BIOMEDICAL ENGINEERING, VOL. 53, No. 12. December 2006).

Among the parameters of vector [PARAM], some may be considered as constant for a given patient. Other parameters, called time-dependent parameters hereafter, are however capable of varying over time. Due to the variability of certain parameters of the system, it may be provided to regularly recalibrate the model used, for example at each acquisition of a new blood glucose value by sensor 101, for example, every 1 to 20 minutes, for example, every 5 minutes, to make sure that the predictions of the model remain relevant. This update of the model, called model personalization, is automatically carried out by the system of FIG. 1, that is, without requiring physically measuring the time-dependent parameters of the system on the patient and then transmitting them to processing and control unit 105.

Figure 3:
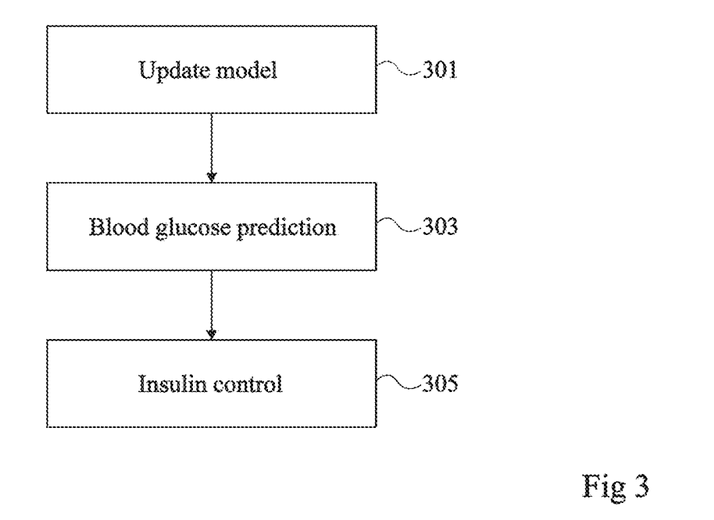
FIG. 3 is a diagram illustrating an example of an automated blood glucose regulation method capable of being implemented by the system of FIG. 1.

FIG. 3 is a diagram illustrating an example of an automated blood glucose regulation method capable of being implemented by the system of FIG. 1.

This method comprises a step 301 of recalibration or update of the model. During this step, processing and control unit 105 implements a method of re-estimation of the time-dependent parameters of the model, taking into account the data relative to the insulin effectively injected by device 103 and the data relative to the real blood glucose measured by sensor 101 for a past observation period of duration $\Delta T$, for example a period from 1 to 10 hours preceding the calibration step. More particularly, during the calibration step, processing and control unit 105 simulates the patient's behavior over the past observation period based on the physiological model (taking into account possible carbohydrate ingestions and insulin injections during this period) and compares the curve of the blood glucose estimated by the model with the curve of the real blood glucose measured by the sensor during this same period. Processing and control unit 105 then searches, for the time-dependent parameters of the model, a set of values leading to minimizing a quantity representative of the error between the blood glucose curve estimated by the model and the real blood glucose curve measured by the sensor during the observation period. As an example, the processing and control unit searches for a set of parameters leading to minimizing an indicator m representative of the area between the curve of the blood glucose estimated by the model and the curve of the real blood glucose measured by the sensor during the observation period, also called standard deviation between the estimated glucose and the real glucose, for example defined as follows:

$$m = \frac{1}{\Delta T} \sum_{t=t_0-\Delta T}^{t_0} |g(t) - gh(t)|^2 \qquad \text{[Math 3]}$$

where t is the discretized time variable, $t0-\Delta T$ corresponds to the time of beginning of the past observation phase, t0 corresponds to the time of end of the past observation phase (for example corresponding to the time of beginning of the calibration of the model), g is the time variation curve of the real blood glucose measured by sensor 101 during period $[t0-\Delta T, t0]$, and gh is the blood glucose curve estimated from the model during period $[t0-\Delta T, t0]$. As a variant, for the calculation of the mean square deviation, variable $\Delta T$ may be replaced with the number of measurements performed during the past observation period. The optimal parameter search algorithm used during this step is not detailed in the present application, the described embodiments being compatible with usual algorithms used in various fields to solve problems of parameter optimization by minimization of a cost function.

It should be noted that during step 301, in addition to the time-dependent parameters of the model, processing and control unit 105 defines a vector [INIT] of initial states (states at time $t_0-\Delta T$) of the state variables of the model, to be able to simulate the patient's behavior from the model. To define the initial states of the state variables of the model, a first possibility comprises making the assumption that, in the period preceding the observation period $[t_0-\Delta T, t_0]$ having the model calibration based thereon, the patient was in a stationary state, with a constant flow of injected insulin, and no dietary intake of carbohydrates. Under this assumption, all the derivatives of the differential equation system may be considered as zero at initial time $t_0-\Delta T$. The values at time $t_0-\Delta T$ of the state variables of the system may then be analytically calculated. To improve the initialization, another possibility comprises making the same assumptions as previously, but adding the constraint that the blood glucose estimated at time $t_0-\Delta T$ is equal to the real blood glucose measured by the sensor. To further improve the initialization, another possibility is to consider the initial states of the state variables of the model as random variables, just as the time-dependent parameters of the model. The initial states of the state variables are then determined in the same way as the time-dependent parameters of the model, that is, processing and control unit 105 searches for a set of values of initial states [INIT] resulting in minimizing a quantity representative of the error between the curve of the blood glucose estimated by the model and the curve of the real blood glucose during the past observation period.

The method of FIG. 3 further comprises, after step 301, a step 303 of prediction, by processing and control unit 105, of the time variation of the patient's blood glucose over a prediction period to come $[t0, t_0+Tpred]$ of duration Tpred, for example, in the range from 1 to 10 hours, based on the physiological model updated at step 301 and taking into account the history of the insulin injected to the patient and the history of carbohydrates ingested by the patient.

The method of FIG. 3 further comprises, after step 303, a step 305 of determination, by processing and control unit 105, taking into account the future blood glucose curve predicted at step 303, of the insulin doses to be injected to the patient for the prediction period to come $[t0, t_0+Tpred]$. At the end of this step, processing and control unit 105 may program injection device 103 to deliver the doses determined during the prediction period $[t0, t_0+Tpred]$.

The sequence of steps 301, 303, and 305 may be repeated at regular intervals, for example, at each new acquisition of a blood glucose value by sensor 101, for example every 1 to 20 minutes, for example, every five minutes.

As a variant, model MODEL may be a non-physiological mathematical model, for example, an ARX-type autoregressive model, in the form of one or a plurality of equations determined by training by the sole observation of the effects of the input variables on output G(t), without taking into account the different known physiological mechanisms operating in the patient's body.

In the above-described system, to guarantee the patient's security, the control of the insulin injection device is not performed based on the output data of model MODEL only. More particularly, model MODEL is used in combination with a security capping algorithm, also called hypominimizer (HM), or hypoglycemia minimizing algorithm, having the function of anticipating and of preventing imminent hypoglycemias by interrupting the insulin flow administered by device 103 and/or by suggesting a resugaring to the patient, that is, a carbohydrate ingestion.

Indeed, in certain situations, the predictions made by mathematical model MODEL may occur not to be sufficiently reliable, whereby the control of insulin injection device 103 based on the predictions made by mathematical model MODEL only does not enable to correctly regulate the patient's blood glucose.

The hypoglycemia minimization capping algorithm, also implemented by processing and control circuit 105, enables to predict an imminent risk of hypoglycemia and, when such a risk is detected, to leave the predictive control operating mode based on the use of mathematical model MODEL, and to decrease or interrupt the flow of insulin injected to the patient, or even to suggest a resugaring to the patient to try avoiding the hypoglycemia.

Figure 4:
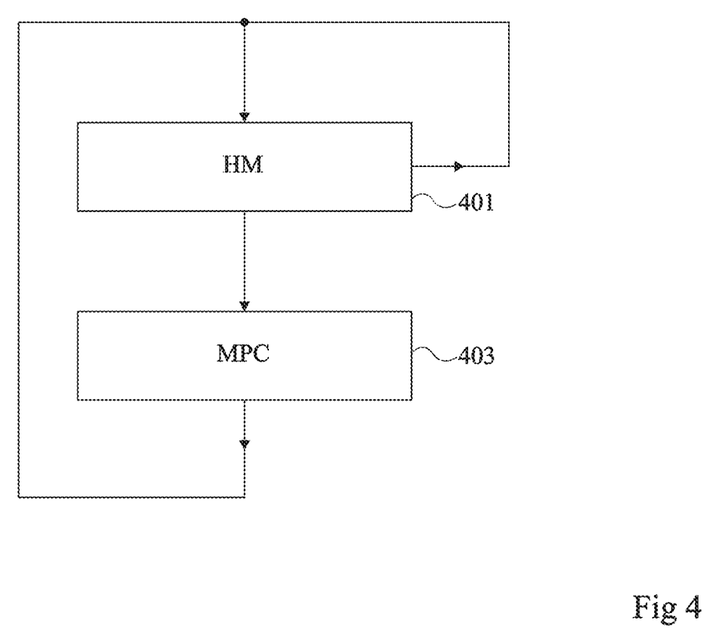
FIG. 4 is a diagram illustrating an example of an embodiment of an automated blood glucose regulation method implemented by the system of FIG. 1.

FIG. 4 is a diagram illustrating in simplified fashion an embodiment of an automated blood glucose regulation method implemented by the system of FIG. 1.

The method of FIG. 4 comprises a step 401 (HM) corresponding to the implementation of the hypoglycemia minimization capping algorithm, and a step 403 (MPC) corresponding to the implementation of a predictive control operation based on use of mathematical model MODEL such as described hereabove in relation with FIGS. 2 and 3.

During step 401, processing and control circuit 105 determines, based on the last data stored for the patient, whether there exists a risk of hypoglycemia in a close future.

If such a risk is detected, processing and control circuit 105 decreases or interrupts the insulin flow administered to the patient by means of device 103, and may further, according to the significance and/or to the imminence of the predicted hypoglycemia, suggest a resugaring to the patient, for example, by means of a user interface device (alarm, display screen, etc.) not detailed herein. Step 401 is then repeated until the risk of hypoglycemia is discarded.

If, during step 401, no risk of hypoglycemia is detected in a close future, processing and control device 105 implements step 403. As an example, step 403 comprises a single iteration of the steps 301, 303, and 305 of the method of FIG. 3. At the end of step 403, step 401 is implemented again.

Step 401 (possibly followed by step 403), is for example repeated at regular intervals, for example, at each new acquisition of a blood glucose value by sensor 101, for example every 1 to 20 minutes, for example, every five minutes.

Figure 5:
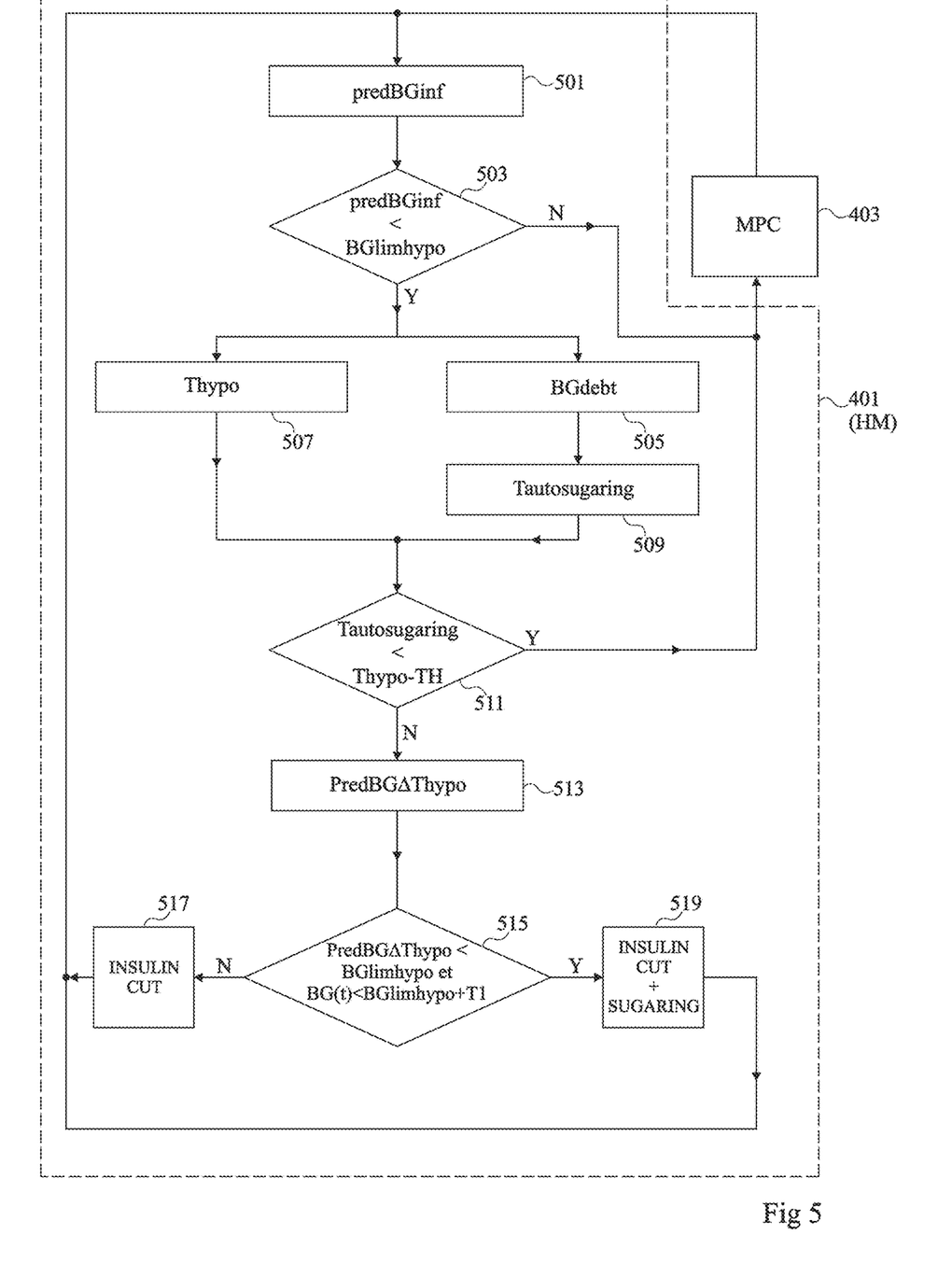
FIG. 5 is a diagram illustrating in further detail an embodiment of the regulation method of FIG. 4.

FIG. 5 is a diagram illustrating in further detail an example of an implementation mode of the regulation method of FIG. 4. More particularly, FIG. 5 illustrates in more detailed fashion an embodiment of the hypoglycemia minimization capping algorithm implemented by processing and control device 105 during step 401 of the regulation method of FIG. 4.

In the example of FIG. 4, step 401 comprises a first step 501 of determination, by processing and control unit 105, of a value predBGinf corresponding to a prediction of the patient's blood sugar at an infinite horizon in the absence of any outer disturbance and particularly in the absence of any new blood glucose ingestion and of any new insulin injection, except for a reference base flow of the patient, which corresponds to a flow specific to the patient, prescribed by their diabetologist and programmed to be injected by device 103 in the absence of any other takeover by the regulation system. Thus, value predBGinf is representative of the blood glucose that the patient will have when all the carbohydrates previously ingested by the patient will have been assimilated and transformed into blood glucose.

Value predBGinf may be determined by using the mathematical model MODEL of FIG. 2, or any other adapted predictive model.

In a preferred embodiment, value predBGinf is defined as follows:

$$predBGinf = BG(t0) - \frac{IOBimpact(t0)}{CR} \text{ with} \quad \text{[Math 4]}$$

$$IOBimpact(t0) = IOB(t0) - COB(t0) * \text{meal\_ratio} \quad \text{[Math 5]}$$

where:
- BG(t0) is the patient's blood glucose at observation time t0, for example corresponding to the last blood glucose value measured by sensor 101;
- IOB(t0) is a value representative, at time to, of the quantity of insulin on board of the patient, that is, of the quantity of insulin still active (that is, still capable of having an effect on the blood glucose) at time to in the patient's body;
- COB(t0) is a value representative, at time t0, of the quantity of carbohydrate on board of the patient, that is, of the portion of the quantity of carbohydrate ingested by the patient still likely, at time t0, to have an effect on the patient's blood glucose;
- meal_ratio is a coefficient representative of the quantity of ingested carbohydrate compensated by an insulin unit (IU) for the patient, for example, in g/IU, IU designating an international insulin unit, that is, the biological equivalent of 0.0347 mg of human insulin;
- CR designates the patient's insulin sensitivity coefficient, representative of the quantity of insulin necessary to decrease the blood glucose by one gram per liter (in IU/g/l); and
- IOBimpact(t0) represents, at time t0, the portion of the quantity of insulin on board IOB(t0) which will result in decreasing the patient's blood glucose with respect to their current blood glucose BG(t0).

Signal IOB(t) is for example calculated by processing and control unit 105 from the injected insulin data i(t) and an action function hIOB representing the time variation of the effect of the injected insulin on the blood glucose absorption. As an example, signal IOB(t) is defined as follows:

$$IOB(t) = \sum_{k=0}^{K} i(t-k) * h_{IOB}(k) \quad \text{[Math 6]}$$

where t is a discretized time variable, K is an integer greater than 1, and k is an integer in the range from 0 to K.

It should be noted that in this example, the IOB is calculated without the patient's reference base flow. In other words, to calculate the IOB, based on the above-mentioned equation Math 6, the considered quantity of injected insulin i(t) is actually the difference between the total quantity iTOT(t) of injected insulin and the reference base flow iBASE(t) prescribed to the patient. This quantity may thus be negative when the patient's insulin flow is interrupted. This explains that the patient's IOB may transit through negative values as will be described in further detail hereafter in relation with FIG. 6.

Signal COB(t) is for example calculated by processing and control unit 105 from the ingested carbohydrate data cho(t) and an action function hCOB representing the time variation of the effect of the ingested carbohydrates on blood glucose. As an example, signal COB(t) is defined as follows:

$$COB(t) = \sum_{k=0}^{K} cho(t-k) * h_{COB}(k) \quad \text{[Math 7]}$$

In the above-mentioned equations Math 6 and Math 7, quantity K defines the duration d for which the history of injected insulin or of ingested carbohydrates is taken into account for the calculation of input variables IOB(t) and COB(t), such that d=K*T, T being the sampling period of the discretized time variable. As an example, duration d is in the range from 1 to 600 minutes, for example, in the order of 300 minutes.

Action functions hIOB and hCOB are for example defined as follows:

$$h_{IOB}(t) = \left[1 + \frac{t}{\tau IOB}\right] e^{-\frac{\tau}{\tau IOB}} \quad \text{[Math 8]}$$

$$h_{COB}(t) = \left[1 + \frac{t}{\tau COB}\right] e^{-\frac{\tau}{\tau COB}} \quad \text{[Math 9]}$$

where τIOB is a time constant, for example in the range from 5 to 120 minutes, for example, in the order of 50 minutes, and where τCOB is a time constant, for example, different from τIOB, for example in the range from 5 to 120 minutes, for example, in the order of 40 minutes.

Once value predBGinf has been determined, processing and control device 105 implements a step 503 of comparison of value predBGinf with a predetermined blood glucose threshold BGlimhypo, corresponding to the threshold below which the patient is considered as suffering from hypoglycemia, for example, in the order of 70 mg/dl.

If, at step 503, value predBGinf is greater than or equal to threshold BGlimhypo (N), it is considered that there is no significant risk of hypoglycemia for the patient in a close future. In this case, step 401 ends and processing and control device 105 implements step 403. In other words, the automated regulation of the patient's blood glucose is performed by using mathematical model MODEL, according to the operating mode described in relation with FIGS. 2 and 3.

If, at step 503, value predBGinf is greater than threshold BGlimhypo (Y), it is considered that there is a risk for the patient to start a hypoglycemia in a close future.

Processing and control device 105 then implements steps 505 and 507 aiming at assessing this risk. More particularly, during step 505, device 105 tries to estimate what the significance or the amplitude of the hypoglycemia will be if nothing is done to stop it and, during step 507, device 105 tries to determine within how much time (starting from time t0), the patient will start a hypoglycemia.

During step 505, processing and control device 105 determines a value BGdebt corresponding to the patient's estimated blood glucose debt, that is, the difference between the blood glucose prediction over an infinite horizon and the blood glucose threshold, defined as follows:

$$BGdebt = BGlimhypo - predBGinf \quad \text{[Math 10]}$$

Value BGdebt corresponds to a blood glucose rate that will have to be compensated to avoid hypoglycemia.

During step 507, it is desired to estimate a time Thypo remaining (from time t0) before the beginning of the hypoglycemia.

For this purpose, processing and control unit 105 determines a negative coefficient nGRC representative of the patient's blood glucose drop, for example in mg/dl/min. The time remaining before the hypoglycemia is then calculated as follows:

$$Thypo = \frac{BGlimhypo - BG(t0)}{nGRC} \quad \text{[Math 11]}$$

As an example, coefficient nGRC may be selected among the following coefficients:
- a coefficient nGRClim representative of the maximum blood glucose drop estimated for the patient;
- a coefficient nGRCmean representative of the average blood glucose drop estimated for the patient; or
- a coefficient nGRCcurrent representative of the current blood glucose drop estimated for the patient.

Coefficients nGRClim and nGRCmean are for example determined from a patient-specific model, constructed based on a history of data of the patient, for example, a history of data recorded by the regulation system over a period of from a plurality of weeks to a plurality of months. At the beginning of the use of the regulation system, before a sufficiently significant data history has been acquired, a generic model (in other words, not specific to the patient), also called population model, may be used to determine coefficients nGRClim and nGRCmean. The population model is for example determined from a database containing the blood glucose history, the insulin injection history, and the carbohydrate intake history of a large number of patients, for example, at least 20 patients, over a relatively long period, for example, from a plurality of weeks to a plurality of months.

Coefficient nGRCcurrent may be determined by extrapolation, for example, linear, of the blood glucose drop measured by sensor 101 during a past observation period, for example in the order of from 10 to 40 minutes.

As a variant, instead of calculating a single estimated value Thypo of the duration remaining before the hypoglycemia, based on one of the three above-mentioned coefficients nGRClim, nGRCmean, and nGRCcurrent, circuit 105 may be configured to calculate three estimated value of the duration remaining before the hypoglycemia Thypolim, Thypomean, and Thypocurrent, based respectively on the three coefficients nGRClim, nGRCmean, and nGRCcurrent.

During a step 509 subsequent to step 505, processing and control device 105 tries to estimate the time within which the blood glucose debt BGdebt estimated during step 505 could be compensated by endogenous glucose production in case of a cutting of the insulin flow injected to the patient. It is indeed established that the cutting of the insulin flow enables to increase the blood glucose due to the fact that the organism, and particularly the liver, naturally produces a quantity of blood glucose called EGP ("Endogenous Glucose Production"). Thus, in the absence of an insulin injection, a diabetic patient will see their blood glucose increase in substantially constant fashion.

During step 509, circuit 105 determines a value Tautosugaring representative of the duration necessary for the natural compensation of the blood glucose debt BGdebt by endogenous production of blood glucose in case of a cutting of the insulin flow. Duration Tautosugaring is calculated as follows:

$$Tautosugaring = \frac{BGdebt}{EGE} \quad \text{[Math 12]}$$

where EGE ("Endogenous Glucose Expansion") is a value representative of the patient's endogenous blood glucose rise rate.

Clinical protocols have been provided to measure a patient's endogenous blood glucose rise rate. These protocols are however constraining and cannot be regularly repeated.

According to an aspect of an embodiment, it is here provided to estimate the patient's EGE rate by means of processing and control device 105 by analysis of the patient's blood glucose history and insulin injection history. This enables to estimate the EGE parameter individually for each patient, and to regularly implement this parameter in the case where its value would vary over time.

Figure 6:
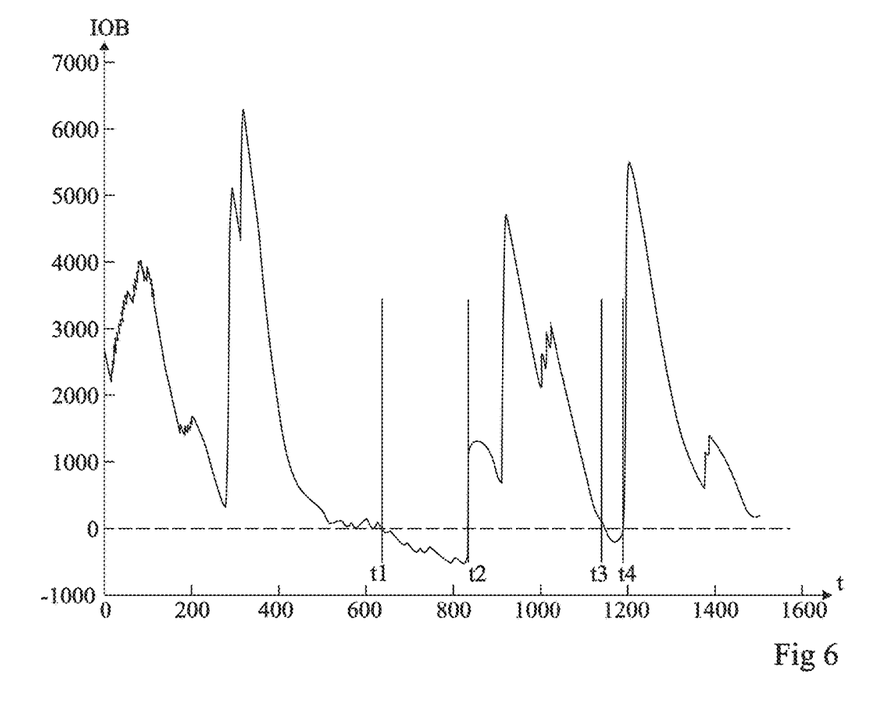
FIG. 6 is a diagram illustrating an example of a method of determination of a value representative of a patient's endogenous glucose production.
Figure 7:
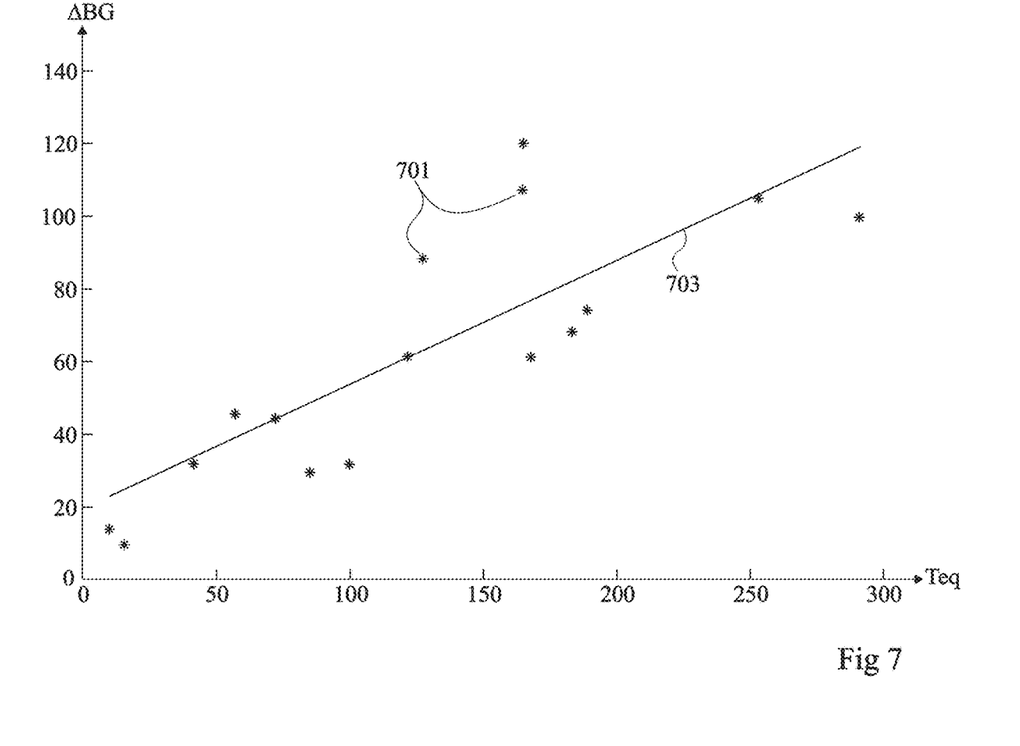
FIG. 7 is another diagram illustrating an example of a method of determination of a value representative of a patient's endogenous glucose production.

The method of estimation of the EGE parameter implemented by device 105 is illustrated in FIGS. 6 and 7.

FIG. 6 is a diagram illustrating the variation over time t (in abscissas, in minutes) of the patient's quantity of insulin on board IOB (in ordinates, in mIU). As previously indicated, the IOB considered in this example is calculated without the patient's reference base flow (it is also spoken of a net IOB), which explains that the patient's IOB can transit through negative values when the insulin flow injected to the patient is interrupted or decreased with respect to the reference base flow, as shown in FIG. 6.

To estimate the patient's endogenous blood glucose rise rate parameter EGE, device 105 identifies measurement events, that is, time ranges during which the patient's IOB is negative, that is, time ranges during which the regulation system has tried to have the patient's blood glucose naturally rise by endogenous glucose production. FIG. 6 shows two time ranges [t1, t2] and [t3, t4] during which curve IOB(t) is negative (with t1<t2<t3<t4).

For each identified measurement event, device 105 calculates a value Insulin_missed representative of the missing quantity of insulin to maintain the blood glucose level constant, defined as follows:

$$\text{Insulin\_missed} = \sum_{t=tstart}^{tend} \frac{d(IOB(t))}{dt} \quad \text{[Math 13]}$$

where tstart and tend respectively designate the time of beginning and the time of end of the measurement event (considering that the insulin activity is the time derivative of the IOB).

Once the missing insulin has been estimated, it may be normalized with respect to the patient's insulin reference base flow (in IU/h) to come down to an equivalent temporal quantity Teq. Value Teq is then representative of the equivalent time of cutting of the patient's reference base flow linked to the event.

Once value Teq has been determined, processing and control circuit 105 measures the patient's blood glucose rise linked to the event, and the patient's blood glucose endogenous increase is deduced therefrom.

FIG. 7 is a diagram showing, for a given patient, the variation, according to the equivalent time of cutting of the reference base flow Teq (in abscissas, in minutes), of the patient's natural blood glucose rise ΔG during the event (in ordinates, in mg/dl). The diagram of FIG. 7 more particularly comprises a cloud of points 701, each point 701 corresponding to a measurement event identified by device 105 in the patient's blood glucose data and IOB history, and showing the pair of values Teq. AG determined by device 105 for this event.

Based on this cloud of points, device 105 determines, by linear regression, a straight line 703 representative of the variation of the patient's endogenous blood glucose rise ΔG according to the equivalent time Teq of cutting of the insulin reference base flow.

The value assigned by processing and control unit 105 to the patient's endogenous blood sugar rise rate parameter EGE corresponds to the slope of straight line 703, in the order of 27 mg/dl/h in the example of FIG. 7.

The value of parameter EGE may for example be recalculated by device 105 for each new occurrence of a measurement event (that is, transition of the patient's IOB through a negative value).

As a variant, rather than selecting the value of parameter EGE as being equal to the slope of curve 703, device 105 may assign parameter EGE a value equal to the smallest blood glucose endogenous rise rate measured for the patient during the different identified measurement events.

At the beginning of the system use, before a significant number of measurement events could have been detected by device 105, device 105 may assign parameter EGE a predetermined fixed value, for example, a value determined according to the above method but based on the JOB history and the blood glucose history of a large number of patients.

Once duration Tautosugaring has been determined, device 105 implements a step 511 of comparison of the duration Tautosugaring determined at step 509 with the duration Thypo determined at step 507. More particularly, in this example, device 105 compares value Tautosugaring with a value Thypo-TH, where TH is a predetermined fixed time margin, for example, in the range from 5 to 30 minutes, for example in the order of from 10 to 15 minutes.

If, at step 511, value Tautosugaring is smaller than value Thypo-TH (Y), it is considered that there is no significant risk of imminent hypoglycemia for the patient, and that the hypoglycemia predicted at step 503 may still be avoided by keeping on regulating the patient's blood glucose based on model MODEL. In other words, the hypoglycemia detected at step 503 is not considered as a short-term menace since the patient's blood glucose debt may still be compensated by interruption of the patient's insulin flow. In this case, step 401 ends and processing and control device 105 implements step 403. In other words, the automated regulation of the patient's blood glucose is performed by using mathematical model MODEL, according to the operating mode described in relation with FIGS. 2 and 3.

If, at step 511, value Tautosugaring is greater than or equal to value Thypo-TH (N), it is considered that there is a risk for the patient to start a hypoglycemia in a close future.

During a step 513, device 105 then makes a new prediction of the patient's future blood glucose, by considering that the flow of insulin injection to the patient is entirely interrupted. More particularly, device 105 calculates a value predBGΔThypo representative of the patient's future blood glucose at time t0+Thypo.

Value predBGΔThypo may be determined by using the model MODEL of FIG. 2, or any other adapted predictive model.

In a preferred embodiment, value predBGΔThypo is defined as follows:

$$predBG\Delta Thypo = BG(t0) - \frac{InsulinConsumed}{CR} + \frac{CHOconsumed}{SugaringRatio} + EGE*Thypo \quad \text{[Math 14]}$$

where $$InsulinConsumed = \sum_{t=t0}^{t0+Thypo} \frac{d(IOB(t))}{dt} \quad \text{[Math 15]}$$

and $$CHOconsumed = \sum_{t=t0}^{t0+Thypo} \frac{d(COB(t))}{dt} \quad \text{[Math 16]}$$

and where SugaringRatio is a coefficient representative of the impact of the ingested carbohydrates on the blood glucose rise, in g/g/l (gram of CHO per g/l of blood glucose).

This prediction enables, at each new iteration of step 401, to verify whether the hypoglycemia is being compensated.

Once value predBGΔThypo has been determined, processing and control device 105 implements a step 515 of comparison of value predBGΔThypo with hypoglycemia threshold BGlimhypo.

At step 515, device 105 further determines whether the patient's current blood glucose BG(t0) is sufficiently distant from hypoglycemia threshold BGlimhypo. More particularly, at step 515, device 105 compares value BG(t0) with a value BGlimhypo+T1, where T1 is a predetermined blood glucose margin, for example in the range from 5 to 20 mg/dl.

If, at step 515, value predBGΔThypo is greater than or equal to threshold BGlimhypo, or if value predBGΔThypo is smaller than threshold BGlimhypo but value BG(t0) is greater than or equal to value BGlimhypo+T1 (N), it is considered that the interruption of the insulin flow may still be sufficient to avoid the hypoglycemia.

In this case, during a step 517 (INSULIN CUT), device 105 controls the full interruption of the insulin flow injected to the patient (including of the patient's reference base flow). Step 401 is then repeated from step 501, for example after an interval in the range from 1 to 20 minutes, for example in the order of 5 minutes, without for a resugaring to be suggested to the patient.

If, at step 515, value predBGΔThypo is smaller than threshold BGlimhypo and value BG(t0) is smaller than value BGlimhypo+T1 (N), it is considered that the hypoglycemia is imminent and that the natural blood glucose rise by endogenous glucose production will not be sufficient to avoid it.

In this case, during a step 519 (INSULIN CUT+SUGARING), device 105 then controls the complete interruption of the insulin flow injected to the patient (including of the patient's reference base flow) and further controls a user interface device (not detailed in the drawings), for example a display screen, an alarm, etc. to indicate to the patient that they must have a carbohydrate intake to avoid hypoglycemia. Step 401 is then repeated from step 501, for example after an interval in the range from 1 to 20 minutes, for example, in the order of 5 minutes.

In the case where, at step 507, circuit 105 calculates three estimated values of the remaining time before the hypoglycemia Thypolim, Thypomean, and Thypocurrent, based, respectively, on the three coefficients nGRClim, nGRCmean, and nGRCcurrent, it may advantageously be provided:
- at step 511, to compare duration Tautosugaring with value ThypoMIN-TH, where ThypoMIN is the shortest of the three durations Thypolim, Thypomean, and Thypocurrent;
- at step 513, to calculate three estimated values predBGΔThypolim, predBGΔThypomean, and predBGΔThypocurrent of the patient's future blood glucose respectively at times t0+Thypolim, t0+Thypomean, and t0+Thypocurrent;
- at step 515, to compare each of the three values predBGΔThypolim, predBGΔThypomean, and predBGΔThypocurrent with value BGlimhypo and to proceed to step 517 (cutting the insulin without offering a resugaring) only if the three values predBGΔThypolim, predBGΔThypomean, and predBGΔThypocurrent are greater than or equal to threshold BGlimhypo or if:
  a) a single one of the three values predBGΔThypolim, predBGΔThypomean, and predBGΔThypocurrent is smaller than threshold BGlimhypo and value BG(t0) is greater than or equal to value BGlimhypo+T1,
  b) two of the three values predBGΔThypolim, predBGΔThypomean, and predBGΔThypocurrent are smaller than threshold BGlimhypo and value BG(t0) is greater than or equal to value BGlimhypo+T2, where T2 is a blood glucose margin greater than margin T1, or
  b) the three values predBGΔThypolim, predBGΔThypomean, and predBGΔThypocurrent are smaller than threshold BGlimhypo and value BG(t0) is greater than or equal to value BGlimhypo+T3, where T3 is a blood glucose margin greater than margin T2.

In the opposite case (Y), a resugaring is suggested to the patient in addition to the insulin cut (step 519).

Figure 8:
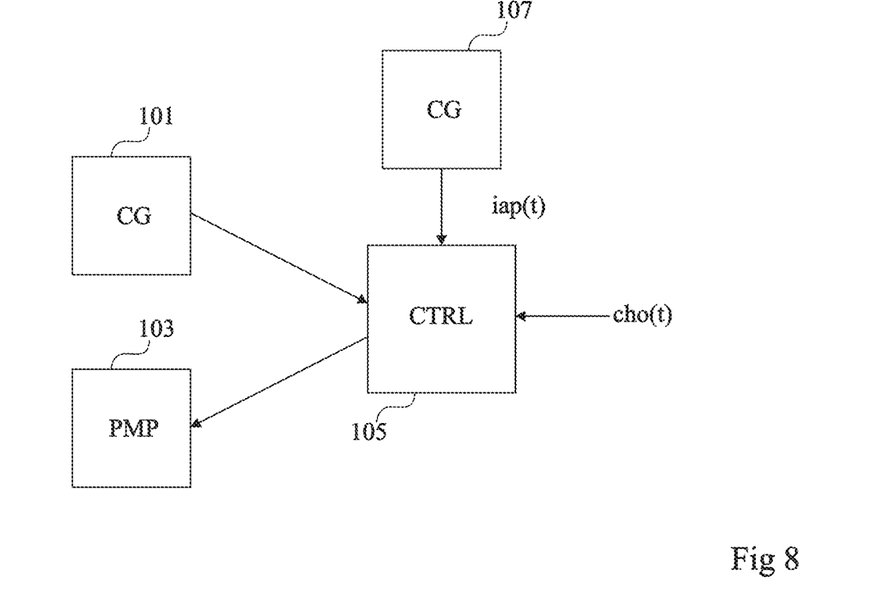
FIG. 8 schematically shows in the form of blocks another example of an automated system of regulation of a patient's blood glucose according to an embodiment.

FIG. 8 schematically shows in the form of blocks another example of an automated system for regulating a patient's blood glucose according to an embodiment. The system of FIG. 8 comprises the same elements as the system of FIG. 1, arranged to cooperate substantially in the same way.

In the example of FIG. 8, the system further comprises a device 107 for measuring a physical activity of the patient. Device 107 is coupled to processing and control unit 105, for example, by a wire link or a radio link (wireless), and communicates to processing and control unit 105 a signal iap(t) representative of the variation over time t of a physical activity of the patient. Device 107 is for example a mobile device carried by the patient all along the day and/or the night.

As an example, device 107 is a simple user interface (not detailed) via which the patient declares their physical activities. As an example, signal iap(t) corresponds to a level of physical intensity declared by the patient via device 107. Device 107 is for example provided with a keyboard enabling the user to input, on a scale from 0 to N, where N is a positive integer, for example, equal to 3, the intensity level of their current physical activity, value 0 corresponding to a physical activity considered as null or negligible, and value N corresponding to the patient's maximum physical activity intensity level.

As a variant, device 107 comprises one or a plurality of sensors capable of measuring quantities representative of the patient's physical activity. As an example, device 107 comprises at least one motion sensor (not detailed in FIG. 8), for example, an accelerometer. Device 107 may further comprise a sensor of the patient's heart rate (not detailed in FIG. 8). In this case, signal iap(t) is for example a signal representative of the patient's energy expenditure, calculated from the output data of the sensor(s) of device 107, for example, as described in the article entitled "Prior automatic posture and activity identification improves physical activity energy expenditure prediction from hip-worn triaxial accelerometry" of M. Garnotel et al. (Journal of Applied Physiology (1985). 2017 Nov. 30), or in the article entitled "An original piecewise model for computing energy expenditure from accelerometer and heart rate signals" of H. Romero-Ugalde et al. (Physiological measurement, 2017 Jul. 28; 38(8): 1599-1615).

As a variant, signal iap(t) may be a combination of a signal measured by means of one or a plurality of sensors of device 107, and of a signal of physical activity intensity declared by the patient by means of a user interface of device 107.

The operation of the system of FIG. 8 is similar to what has been previously described, with the difference that, in the system of FIG. 8, processing and control device 105 takes into account signal iap(t) during step 401 of the blood glucose regulation method.

As an example, at step 501 of prediction of the blood glucose at the infinite horizon, the coefficient(s) nGRC, nGRClim, nGRCmean, and nGRCcurrent representative of the patient's blood glucose drop rate are adapted according to the patient's physical activity signal iap(t). In particular, the blood glucose drop rate values used will be selected to be all the higher as the physical activity iap(t0) is high.

Further or alternately, a new insulin action time constant, decreased to model the increase of the insulin action speed in the presence of a physical activity, may be used. As an example, the time constant τIOB of the above-mentioned equation Math 8 may be replaced with a time constant τIOBap=f(iap(t)), where f is a decreasing function modeling the increase of the insulin action speed (and thus the decrease of the insulin action time constant) when the intensity of physical activity iap(t) increases.

As an example, function f is defined as follows:

$$\tau IOBap = f(iap(t)) = \frac{C}{iap(t)} \qquad \text{[Math 17]}$$

where C is a parameter in the range from 1 to 100, for example, substantially equal to 30.

It should be noted that the calculation is not limited to the above-mentioned examples of mathematical formulas [Math 6] and [Math 8] to define signal IOB(t). More generally, this calculation mode may be used whatever the formula used to define signal IOB(t), comprising the multiplication of a signal representative of the insulin injected to the patient by a decreasing exponential of constant τIOBap (in form e^(−t/τIOBap)).

Various embodiments and variants have been described. Those skilled in the art will understand that certain features of these various embodiments and variants may be combined, and other variants will occur to those skilled in the art. In particular, the described embodiments are not limited to the numerical examples mentioned in the present description.

It should further be noted that in the above described examples, the automated blood glucose regulation method implemented at step 403, based on the use of predictive model MODEL, may be replaced with any other automated blood glucose regulation method, for example, a method using an algorithm of decision-making matrix type to determine the doses of insulin to be administered to the patient, according to various observed parameters such as the current blood glucose level measured by sensor 101, or also the variation speed (or slope) of the blood glucose over a past period.

Further, in the method of FIG. 5, at step 519, instead of suggesting a resugaring to the patient and of interrupting the insulin flow injected to the patient, it may as a variant be provided to suggest a resugaring to the patient (via a user interface device) without cutting the insulin flow injected to the patient. Indeed, in practice, the effect of the resugaring on the patient's blood glucose is much faster than the patient's endogenous blood glucose rise, so that, in case of a resugaring, the hypoglycemia may be avoided without interrupting the patient's insulin flow.

The invention claimed is:

1. Automated system of regulation of a patient's blood glucose, comprising:
   a blood glucose sensor;
   an insulin injection device; and
   a processing and control unit,
   wherein the processing and control unit is configured to implement a hypoglycemia minimization method comprising the steps of:
   a) detecting a possible hypoglycemia to come based on blood glucose measurements supplied by the blood glucose sensor;
   b) determining a value BGdebt representative of a blood glucose debt to be compensated to avoid the hypoglycemia detected at step a) and a value Thypo representative of the time remaining before the beginning of the hypoglycemia detected at step a);
   c) determining a value Tautosugaring representative of the duration necessary to enable the patient to compensate for the blood glucose debt BGdebt determined at step b) by endogenous glucose production;
   d) comparing the value Tautosugaring determined at step c) with a value Thypo-TH, where TH is a predetermined time margin; and
   e) when it is determined at step d) that value Tautosugaring is greater than or equal to value Thypo-TH, controlling the interruption of the insulin flow injected to the patient by the insulin injection device and/or starting an alert via a user interface device of the system to indicate to the patient that they must perform a carbohydrate ingestion.

2. System according to claim 1, wherein, at step c), the processing and control unit determines a value EGE representative of the patient's endogenous blood glucose rise rate, value Tautosugaring then being calculated by the processing and control unit according to the following formula:

$$Tautosugaring = \frac{BGdebt}{EGE} \quad \text{[Math 18]}$$

3. System according to claim 2, wherein, at step c), value EGE is calculated by the processing and control unit by analysis of the patient's blood glucose history and insulin injection history.

4. System according to claim 1, wherein, at step e), the processing and control unit determines a value predBGΔThypo estimative of the patient's future blood glucose at the end of period Thypo.

5. System according to claim 4, wherein the processing and control unit is configured to, after step e), implement the steps of:
   f) comparing value predBGΔThypo with a predetermined hypoglycemia threshold BGlimhypo;
   g) when it is determined at step f) that value predBGΔThypo is smaller than hypoglycemia threshold BGlimhypo, comparing a value BG(t0) representative of the patient's current blood glucose, measured by the sensor, with a value BGlimhypo+T1, where T1 is a predetermined blood glucose margin; and
   h) when it is determined at step g) that value BG(t0) is smaller than value BGlimhypo+T1, start an alert via a user interface device of the system to indicate to the patient that they must perform a carbohydrate ingestion.

6. System according to claim 1, wherein, at step b), the processing and control unit determines three values Thypolim, Thypomean, and Thypocurrent estimative of the time remaining before the beginning of the hypoglycemia, respectively based on a maximum blood glucose drop rate nGRClim determined for the patient, on an average blood glucose drop rate nGRCmean estimated for the patient, and on a current blood glucose drop rate nGRCcurrent estimated for the patient.

7. System according to claim 6, wherein the processing and control unit is configured to, at step d), compare duration Tautosugaring with a value ThypoMIN-TH, where ThypoMIN is the shortest of the three durations Thypolim, Thypomean, and Thypocurrent.

8. System according to claim 7, wherein the processing and control unit is configured to, at step e), calculate three values predBGΔThypolim, predBGΔThypomean, and predBGΔThypocurrent estimative of the patient's future blood glucose respectively at the end of period Thypolim, at the end of period Thypomean, and at the end of period Thypocurrent.

9. System according to claim 8, wherein the processing and control unit is configured to, after step e), implement the steps of:
   f) comparing each of the three values predBGΔThypolim, predBGΔThypomean, and predBGΔThypocurrent with a predetermined hypoglycemia threshold BGlimhypo; and
   g') if a single one of the three values predBGΔThypolim, predBGΔThypomean, and predBGΔThypocurrent is smaller than threshold BGlimhypo, suggesting a resugaring carbohydrate ingestion to the patient only if a value BG(t0) representative of the patient's current blood sugar is smaller than a value BGlimhypo+T1, where T1 is a predetermined blood sugar margin, if two of the three values predBGΔThypolim, predBGΔThypomean, and predBGΔThypocurrent are smaller than threshold BGlimhypo, suggesting a carbohydrate ingestion to the patient only if value BG(t0) is smaller than a value BGlimhypo+T2, where T2 is a determined blood glucose margin greater than margin T1, and if the three values predBGΔThypolim, predBGΔThypomean, and predBGΔThypocurrent are smaller than threshold BGlimhypo, suggesting a carbohydrate ingestion to the patient only if value BG(t0)

is smaller than a value BGlimhypo+T3, where T3 is a predetermined blood glucose margin greater than margin T2.

10. System according to claim 1, further comprising a device for measuring a physical activity of the patient coupled to the processing and control unit and communicating to the processing and control unit a signal iap(t) representative of the time variation of a physical activity of the patient.

11. System according to claim 10, wherein the processing and control unit takes into account signal iap(t) to detect a possible hypoglycemia to come at step a) and/or to determine value Tautosugaring at step c).

12. System according to claim 11, wherein, at step c), the processing and control unit determines a signal IOB(t) representative of the patient's quantity of insulin on board, defined by the multiplication of a signal representative of the quantity of insulin injected to the patient by a decreasing exponential of time constant τIOBap, time constant τIOBap being a decreasing function of signal iap(t), modeling the increase of the speed of action of insulin when the intensity of the physical activity increases.

13. System according to claim 12, wherein time constant τIOBap is defined as follows:

$$\tau IOBap = \frac{C}{iap(t)} \quad \text{[Math 19]}$$

where C is a parameter in the range from 1 to 100.

* * * * *

UNITED STATES PATENT AND TRADEMARK OFFICE
CERTIFICATE OF CORRECTION

Page 1 of 1

PATENT NO. : 12,144,965 B2
APPLICATION NO. : 17/414901
DATED : November 19, 2024
INVENTOR(S) : Romain Blanc et al.

It is certified that error appears in the above-identified patent and that said Letters Patent is hereby corrected as shown below:

In the Claims

In Claim 9, at Column 18, Lines 53-56:
"suggesting a resugaring carbohydrate ingestion to the patient only if a value BG(t0) representative of the patient's current blood sugar"

Should read:
--suggesting a carbohydrate ingestion to the patient only if a value BG(t0) representative of the patient's current blood sugar--

Signed and Sealed this
Twenty-fifth Day of March, 2025

Coke Morgan Stewart
*Acting Director of the United States Patent and Trademark Office*